United States Patent [19]

Matsuda et al.

[11] 3,960,662

[45] June 1, 1976

[54] PROCESS FOR THE PRODUCTION OF 7-AMINO-CEPHEM COMPOUNDS

[75] Inventors: Tetsuo Matsuda; Tsutomu Yamaguchi, both of Tagata; Tadashiro Fujii; Kunio Matsumoto, both of Mishima; Masataka Morishita, Tagata; Mitsuru Fukushima, Shizuoka; Yuzo Shibuya, Tagata, all of Japan

[73] Assignee: Toyo Jozo Kabushiki Kaisha, Japan

[22] Filed: Jan. 23, 1975

[21] Appl. No.: 543,639

[30] Foreign Application Priority Data
Jan. 23, 1974 Japan................................ 49-10471

[52] U.S. Cl..................................... 195/29; 195/96
[51] Int. Cl.$^2$......................................... C12D 13/06
[58] Field of Search................................ 195/29, 96

[56] References Cited
UNITED STATES PATENTS
3,749,641   7/1973   Takahashi et al..................... 195/29

*Primary Examiner*—Alvin E. Tanenholtz
*Attorney, Agent, or Firm*—Young & Thompson

[57] ABSTRACT

7-Amino-cephem compounds are produced from 7-substituted-cephem compounds by the enzymatic action of microorganisms *Comamonas sp.* SY-77-1 FERM-P 2410 or *Pseudomonas ovalis* ATCC 950.

1 Claim, No Drawings

PROCESS FOR THE PRODUCTION OF 7-AMINO-CEPHEM COMPOUNDS

This invention relates to a process for the production of 7-amino-cephem compounds. More particularly, this invention concerns a microbiological process for the production of 7-amino-cephem compounds of the formula

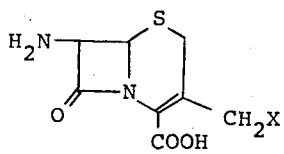

[I]

wherein X represents hydrogen, hydroxy, acetoxy, or a nucleophilic residual group from cephalosporin analogues.

We have found that a microorganism belonging to genus Comamonas strain SY-77-1 separated from soil samples has an activity to produce 7-amino-cephem compounds from a compound of the formula

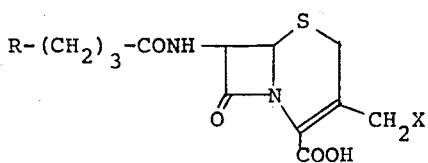

[II]

wherein R is —COOH or —COCOOH and X has the same meanings hereinabove, by splitting an amide linkage thereof.

The microorganism described hereinabove has the following taxonomical properties.

A. Morphology

Observations were taken by optical or electron microscope on bouillon agar slant culture at 30°C.
1. Form and size: short rod, round end, 0.1 - 0.3 x 0.3 - 0.5 μ.
2. Metamorphosis: single or short chain, no capsule.
3. Motility: yes, flagellate.
4. Spore: no sporulation.
5. Gram's stain: negative.
6. Acid-fastness: negative.

B. Growth conditions on several media

1. Bouillon agar plate (30°C., 24 hours): colony round; convex rising; smooth surface; wavy edge; white to slight yellowish white; slightly sticky; translucent to opaque; no dispersion.
2. Bouillon agar slant (30°C., 24 hours): good growth; linear growth; smooth surface; lustrous; moist; opalescent to faint yellowish white surface; translucent to opaque; medium no color change.
3. Bouillon (30°C., 1–3 days): homogeneously turbid; trace precipitation; thready suspension by shaking; no film and ring.
4. Bouillon gelatine stab (30°C., 24 hours): linear growth along stab line, especially on middle to bottom.
5. Soybean agar slant (30°C., 24 hours): good growth; the same as on bouillon agar, smooth surface; lustrous.
6. Potato agar slant: good growth; white colony surface; smooth surface; slightly sticky; translucent to opaque; moist; lustrous; no pigment formation.
7. Litmus milk (30°C., 25 days): almost no liquefaction.
8. Glucose bouillon agar slant (30°C., 24 hours): better growth as compared with bouillon agar slant; slightly sticky.
9. Glucose nitrate agar slant (30°C., 1–3 days): almost no growth.
10. Tyrosine agar slant (30°C., 48 hours): growth; medium slightly turns to brown.
11. Manitol-yeast extract agar plate (30°C., 48 hours): good growth; white to faint yellow; smooth surface; moist; convex; medium no color change.
12. Bouillon agar plate, 7% NaCl added (30°C., 10 days): almost no growth.
13. Glycelin-peptone agar plate (30°C., 3 days): good growth; smooth surface; lustrous; convex; medium turns brown.
14. Milk agar plate (30°C., 5 days): no casein hydrolysis.
15. Taurocholate agar plate (30°C., 15 days): no growth.

C. Physiological properties

1) Nitrate reduction — 
2) Denitrification — 
3) Methyl red test — (yellow)
4) Voges-Proskauer's reaction +
5) Indol formation —
6) Hydrogen sulfate formation —
7) Starch hydrolysis —
8) Utilization of citrate +
9) Utilization of inorganic nitrogen source — no utilization of nitrate.
10) Pigment formation — depend on media.
11) Urease —
12) Oxidase +
13) Catalase +
14) Gelatin liquefaction —
15) Arginine hydrolysis —
16) Gluconate oxidation —
17) Growth range: growth: pH 5–12; 5–42°C. optimum growth: pH 7.0–8.5; 28–35°C.
18) Aerobic or anaerobic: aerobic.
19) O-F test: no change on O-type and F-type test.
20) Fermentation of carbohydrate:

|  | Acid Formation | Gas Formation |
|---|---|---|
| L-arabinose | — | — |
| D-xylose | — | — |
| D-glucose | — | — |
| D-mannose | — | — |
| D-fructose | — | — |
| D-galactose | — | — |
| Maltose | — | — |
| Sucrose | — | — |
| Lactose | — | — |
| Trehalose | — | — |
| Sorbitol | — | — |
| Mannitol | — | — |
| Inositol | — | — |
| Starch | — | — |

When the taxonomical situation of the microorganism strain SY-77-1 having the above-mentioned mycological properties was examined with reference to *Manual for the Identification of Medical Bacteria*, by Cowan and Steel (Ed. 1965) and *Bergey's Manual of Determi-*

*native Bacteriology* (7th Ed. 1961) comparing with type cultures of related strains, it was determined that the strain belonged to the genus Comamonas. Accordingly, the inventors compared the strain SY-77-1 with the type culture obtained from American Type Culture Collection (ATCC) to recognize that the strain was similar to *Comamonas terrigena* but was different therefrom in the point that the strain SY-77-1 had strong activity for splitting an amide-linkage of compound II.

From the above, it will be recognized that the strain SY-77-1 is a new strain belonging to the genus Comamonas and referred to *Comamonas sp.* SY-77-1. This strain has been deposited under the number "FERM-P 2410" in the Research Institute for Microbiological Industry and Technology, Agency of Industrial Science and Technology, Japan, and also has been deposited in the U.S. Department of Agriculture, ARS, Northern Utilization Research and Development Division and has been assigned the numerical designation NRRL B-8070.

We have also found that *Pseudomonas ovalis* ATCC 950 has the same activity.

Thus, the present invention is a process for producing 7-amino-cephem compounds of formula I (hereinafter designated as amino compound I), comprising deacylating a compound of formula II by treatment in the presence of an aqueous medium with a microbial culture or a preparation thereof having an activity for deacylating compound II to form compound I derived from the culture of a deacylating enzyme-producing microbial strain.

An object of the present invention is to provide a novel process for producing 7-amino-cephem compounds from analogous compounds of cephalosporin C microbiologically.

Another object of the present invention is to provide important intermediates for the production of pharmaceutically valuable cephalosporin derivatives.

In the deacylating reaction of the present invention, microorganisms belonging to genus *Comamonas* or genus *Pseudomonas* having the deacylating activity to form compound I from compound II are used.

In order to obtain higher activity to form amino compound I from compound II (hereinater this activity will be designated as N-deacylating activity), known mutation methods for treating bacteria such as selective treatment of strains by ultra violet, X-ray and mutagenic agents, and selection of media and fermentation conditions may advantageously be applied.

Examples of the microorganisms having N-deacylating activity hereinabove are:

*Comamonas sp.* SY-77-1 FERM-P 2410 and
*Pseudomonas ovalis* ATCC 950.

The production of amino compound I using the microorganisms having N-deacylating activity can be achieved by culturing the said microorganisms and treating compound II with the microbial culture or preparation thereof.

The cultivation of the microorganisms can be advantageously carried out under aerobic conditions, more preferably by submerged aeration culture. Nutrient media may include an assimilable source of carbon, an assimilable source of nitrogen and salts. The culturing temperature is preferably 25°–37°C. and the culturing period is generally 2–10 days and at the time when the N-deacylating activity reaches a maximum, the cultivation should naturally be terminated.

The thus-obtained microbial culture or preparation thereof can be used for the N-deacylating reaction on compound II. The preparation of the microbial culture means the treated cultured mass to increase the N-deacylating activity for the production of amino compound I, and includes, for example, due to an endoenzymatic property of N-deacylating activity, washed microbial cells collected from culture mass, cell-free extract such as ground or sonicated cells, cell-lysate treated with buffer solution or cetylpyridinium chloride, purified or partially purified N-deacylating enzyme obtained from cell-free extract by known methods such as salting out, chromatography or the like, immobilized enzyme preparations or microcapsules containing microbial cells or preparations thereof having N-deacylating activity.

The microcapsules may preferably be a three-dimensional structure (gel structure) consisting of semipermeable membrane wall polymer, which does not inhibit N-deacylating activity, covering the core substance of the N-deacylating active preparation.

Examples of encapsulation methods are, for example, the orifice method such that the core substance is dissolved or dispersed in a water-miscible solvent dissolving the semipermeable membrane-forming wall polymer in aqueous medium (Japan. Pat. Open. No. 49-25128); the complex emulsion method in an aqueous vehicle such as dissolving the wall polymer in a water-immiscible solvent which has a boiling point lower than that of water and vapor pressure higher than that of water, which does not inactivate the N-deacylating activity, thereafter dispersing a core substance therein and the said dispersed solution is dropped to suspend into an aqueous solution containing a surface active agent or protective colloid, then removing the solvent to form microcapsules (Japan. Pat. Publ. No. 47-43803, Japan. Pat. Open. No. 49-49679); microcapsulation and solvent removal by non-solvent emulsion, for example dispersing or dissolving a core substance in an organic solvent having a dissolved wall polymer therein, emulsifying said solution in a vehicle which is poorly miscible with the solvent of said wall polymer solution to prepare an emulsion, adding to the emulsion a non-solvent for the wall polymer, the non-solvent for the wall polymer being miscible with the solvent for the wall polymer but miscible or poorly miscible with the vehicle and inhibiting the N-deacylating activity, thereby to form microcapsules (French Pat. No. 2,166,062); and the complex emulsion method in a lipophylic vehicle, for example, dissolving the wall polymer to form a solvent, said solvent being poorly miscible with the vehicle, miscible with water, having a boiling point lower than that of water and inhibiting the N-deacylating activity, dissolving or dispersing a core substance in the solution, emulsifying the said resulting solution in a vehicle comprising liquid paraffin or a silicone oil, and removing the organic solvent to form microcapsules (U.S. Pat. No. 3,714,065 ). The N-deacylating reaction of compound II is generally conducted in an aqueous medium, preferably at pH 6–8. Alternatively water insoluble microbial cells or a preparation thereof is used in the form of a suspension, or in the form of a column wherein compound II is N-deacylated by passing the aqueous solution of compound II through the said column. The reaction period is generally 3–30 hours and it should be terminated when the production of amino compound I reaches a maximum. The reaction temperature may be 20°–45°C., preferably 30°–37°C. Substrate concentration is dependent on the N-acylating activity and it may be generally 0.1 – 5%.

The starting material compound II of the present invention can be prepared by any known process. For example, compound II having a COOH group in R can be prepared from the compound of the formula

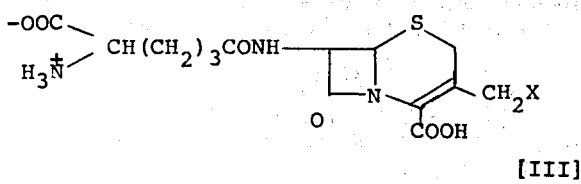

[III]

wherein X has the same meaning hereinabove, or a salt thereof by the action of D-amino acid oxidase derived from microorganisms *Trigonopsis variabiris* etc. under aerobic conditions (British Pat. No. 1,272,769); the compound III or a salt thereof is treated with activated cells of *Trigonopsis variabiris* or *Fusarium sp.* (Japan. Pat. Open. No. 47-39595 and Japan. Pat. Appln. No. 49-117,205). Compound II having a -COCOOH group in R can be prepared from compound III in the presence of catalase activity and D-amino acid oxidase activity.

The substituent X in formula II represents hydrogen, hydroxy, acetoxy or a nucleophilic residual group which can be formed from cephalosporin C by any known method. For example a compound III having hydrogen as group X is prepared by catalytic reduction in the presence of palladium-carbon (U.S. Pat. No. 3,124,576); a compound III having hydroxy as group X is prepared by the action of esterase (Japan. Pat. Publ. No. 42-7553); a compound III having a nucelophilic residual group as group X is prepared by treatment with a weak basic heterocyclic tertiary amine such as pyridine (Japan. Pat. Publ. No. 38-26179) or by other methods (Japan. Pat. Publ. Nos. 39-17926, 41-4714, 43-5010, 42-1305, 46-14735, 46-13025, 46-15951 and 40-9155).

Compound II can be used in the form of a water-soluble salt such as sodium, potassium or ammonium salt.

The thus-formed amino compound I can be isolated and purified by the known methods such as column chromatography, ion-exchange, precipitation or the like.

Assay method of amino compound I:

Aliquot of reaction mixture is adjusted to pH 2.5 with 1 N HCl and after the said solution is washed three times with half the amount of butyl acetate, is adjusted to pH 7.5 with 1 N NaOH. An aliquot amount thereof is reacted with phenylacetyl chloride and assayed on *Bacillus subtilis* PCI 211 for 16 hours at 37°C.

Thin layer chromatography (TLC):
Carrier: silica gel pre-coated.

Developer I: n-BuOH : Acetic acid : water (3:1:1)
II: n-BuOH : Acetic acid : pyridine : water (15:3:10:12)
III: n-BuOH : Acetic acid : formaldehyde : water (3:1:5:1)

The following examples illustrate the invention but are not to be construed as limiting.

EXAMPLES 1 – 5

100 ml. of an aqueous medium (pH 7.0) consisting of meat extract 0.5%, peptone 1%, yeast extract 0.1%, glutaric acid 0.05% and NaCl 0.5% were introduced into a 500 ml. Erlenmyer flask, sterilized at 120°C. for 15 minutes, inoculated with *Comamonas sp.* SY-77-1 FERM-P 2410 and rotary shake cultured at 30°C. for 8 days. After cultivation, the cultured broth was centrifuged at 12,000 rpm for 10 minutes under cooling to collect bacterial cells. The said mass was suspended in 50 ml. of 0.1 molar phosphate buffer solution (pH 7.0). Therein were added 50 ml. of 0.1 mole phosphate buffer (pH 7.0) containing 3% of 3-acetoxymethyl-7-(4-carboxybutaneamide)-ceph-3-em-4-carboxylic acid and incubated at 37°C. for 10 hours to obtain amino compound I. Cultivation of bacteria in the same manner was repeated and each of the following substances was incubated therewith: 3-methyl-7-(4-carboxybutaneamide)-ceph-3-em-4-carboxylic acid; 3-hydroxymethyl-7-(4-carboxybutaneamide)-ceph-3-em-4-carboxylic acid; N-[7-(4-carboxybutaneamide)-ceph-3-em-3-yl-methyl]-pyridinium-4-carboxylate; and 7-(4-carboxybutaneamide)-3-(5-methyl-1,3,4-thiadiazol-2-yl)-thiomethyl-ceph-3-em-4-carboxylic acid.

The results are shown in the table below:

| Example | X | Amino compound [I] (R=—COOH) formation ratio % | TLC Rf | solvent system |
|---|---|---|---|---|
| 1 | H | 72 | 0.32 | I |
| 2 | —OCOCH₃ | 53 | 0.15 | I |
| 3 | —OH | 64 | 0.33 | II |
| 4 | -N⟨⟩ | 58 | 0.23 | III |
| 5 | -S-(N-N/S)-CH₃ | 50 | 0.17 | I |

The amino compounds were identified by thin layer chromatography with ninhydrin developer, ultra violet and bioassay.

EXAMPLES 6 – 9

In Examples 1 - 5, 3-acetoxymethyl-7-(4-carboxybutaneamide)-ceph-3-em-4-carboxylic acid and the others were replaced by the following compounds:

3-methyl-7-(5-carboxy-5-oxopentaneamido)-ceph-3-em-4-carboxylic acid;

3-acetoxymethyl-7-(5-carboxy-5-oxopentaneamido)-ceph-3-em-4-carboxylic acid;

3-hydroxymethyl-7-(5-carboxy-5-oxopentaneamido)-ceph-3-em-4-carboxylic acid; and N-[7-(5-carboxy-5-oxopentaneamido)-ceph-3-em-3-yl-methyl]-pyridinium-4-carboxylate.

The results are shown in the table below:

| Example | X | Amino compound [I] (R = —COCOOH) formation ratio % | TLC Rf | Solvent system |
|---|---|---|---|---|
| 6 | H | 65 | 0.32 | I |
| 7 | —OCOCH₃ | 50 | 0.15 | I |
| 8 | —OH | 58 | 0.34 | II |
| 9 | -N⟨⟩ | 52 | 0.23 | III |

EXAMPLES 10 – 13

100 ml. of an aqueous medium (pH 7.0) consisting of meat extract 0.5%, peptone 1%, yeast extract 0.1%, glutaric acid 0.05% and NaCl 0.5% were introduced into a 500 ml. Erlenmyer flask, sterilized at 120°C. for 15 minutes, inoculated with *Pseudomonas ovalis* ATCC 950 and rotary shake cultured at 30°C. for 8 days. After cultivation, the cultured broth was centrifuged at 12,000 rpm for 10 minutes under cooling to collect bacterial cells. The said cultured cells were suspended in 50 ml. of 0.1 molar phosphate buffer (pH 7.0). Cultivation was repeated in the same manner and the prepared cells suspended. The cell suspensions were incubated at 37°C. for 10 hours with each substance (2% in 0.1 mole phosphate buffer solution) shown in the table below:

Compound [II]:
3-methyl-7-(4-carboxybutaneamido)-ceph-3-em-4-carboxylate;
3-hydroxymethyl-7-(4-carboxybutaneamido)-ceph-3-em-4-carboxylate;
3-acetoxymethyl-7-(4-carboxybutaneamido)-ceph-3-em-4-carboxylate; and
N-[7-(4-carboxybutaneamido)-ceph-3-em-3-yl-methyl]-pyridinium-4-carboxylate.

The results were as follows:

| Example | X | amino compound [I] Rf on TLC |
|---|---|---|
| 10 | H | 0.33 (solvent system I) |
| 11 | —OH | 0.33 (solvent system II) |
| 12 | —OCOCH$_3$ | 0.15 (solvent system I) |
| 13 | —N⟨phenyl⟩ | 0.22 (solvent system III) |

EXAMPLE 14

*Comamonas sp.* SY-77-1 FERM-P 2410 was cultured in the same manner as in Example 4 to obtain 6 l. of cultured broth. The cells were collected by centrifuging at 12,000 rpm for 10 minutes and washed. The thus-obtained cells were suspended in 0.1 molar phosphate buffer (pH 7.0) to produce a 300 ml. suspension. Therein was added 15 ml. of cationic surface active agent, stirred at room temperature for 30 minutes, then centrifuged at 10,000 rpm for 10 minutes to obtain 288 ml. of supernatant.

The supernatant was dialyzed in 0.1 molar phosphate buffer solution (pH 7.0) using a cellophane tube at 4°C. for 48 hours. 300 ml. of dialysate having N-deacylating activity were obtained.

The thus-obtained dialysate is included in the scope of the preparation of microbial culture of the present invention and it may be prepared as a microcapsulated preparation, a powdered preparation by drying, by lyophilization or by ammonium sulfate precipitation.

Also *Pseudomonas ovalis* can be treated in the same manner.

EXAMPLE 15

3 g. of cellulose acetate (triacetate form) were dissolved in 100 ml. of methylenechloride. 3 g. of cultured cells of *Comamonas sp.* SY-77-1 FERM-P 2410, obtained by the same manner as in Example 1, suspended in distilled water, were emulsified therein. The thus-obtained emulsion was stirred, dispersed in 800 ml. of 2% gelatin aqueous solution at room temperature and further stirred until the methylene chloride was evaporated to obtain microcapsules (diameter 0.1 – 0.3 mm.) containing *Comamonas sp.* SY-771 FERM-P 2410. These microcapsules can be used for the production of amino compound I as hereinbelow exemplied.

EXAMPLE 16

Example 15 was repeated except that 2 g. of cellulose acetate, 70 ml. of methylene chloride and 2 g. of *Pseudomonas ovalis* ATCC 950 were used. Microcapsules containing the bacteria were obtained.

EXAMPLE 17

Example 15 was repeated, except that 20 ml. of supernatant having N-deacylating activity obtained in Example 14 were used instead of 3 g. of Comamonas cells suspended in 20 ml. of water to obtain microcapsules of the same size.

EXAMPLE 18

21.9 g. (wet weight) of microcapsules obtained in Example 15 were packed in a column with a jacket (2 × 9.6 cm. V=30 ml.) and washed with 0.1 molar phosphate buffer (pH 7.0). 840 ml. of a solution of 3-acetoxymethyl-7-(4-carboxybutaneamide)-3-cephem-4-carboxylic acid in 0.1 molar phosphate buffer (9.92 mg./ml.) were charged at SV about 0.4. 865 ml. of eluate containing 7-ACA were obtained (yield 84.5%) and then concentrated to 80 ml. after adjusting to pH 3.2. The concentrate was allowed to stand overnight at 4°C. to precipitate the 7-ACA. (Yield 4.6 g., purity 86.2%).

EXAMPLE 19

Example 18 was repeated, except that the microcapsules containing *Comamonas sp.* SY-77-1 FERM-P 2410 were replaced by the microcapsules containing *Pseudomonas ovalis* ATCC 950 obtained in Example 16 and 1% solutions of the substances listed below were used instead of the substrate in Example 18 to obtain amino compounds I hereinbelow.

| Substance | Yield of Compound [I] |
|---|---|
| 3-methyl-7-(4-carboxybutaneamide)-3-cephem-4-carboxylate: | 84.2% |
| 3-hydroxymethyl-7-(4-carboxybutaneamide)-3-cephem-4-carboxylate: | 83.1% |
| N-[7-(4-carboxybutaneamide)-3-cephem-3-yl-methyl]-pyridinium-4-carboxylate: | 79.2% |

EXAMPLE 20

In Example 18, the microcapsule containing *Comamonas sp.* SY-77-1 FERM-P 2410 were replaced by the microcapsules containing supernatant having N-deacylating activity obtained in Example 17, and the substrate was replaced by a 1% solution of 3-acetoxymethyl-7-(4-carboxybutaneamide)-3-cephem-4-carboxylate, 3-methyl-7-(5-carboxy-5-oxopentaneamide)-3-cephem-4-carboxylate and 3-hydroxymethyl-7-(5-carboxy-5-oxopentaneamide)-3-cephem-4-carboxylate to obtain amino compound I of yield 87.5%, 78.8% and 79.5%, respectively.

Having described our invention, we claim:
1. A process for the production of 7-amino-cephem compounds of the formula

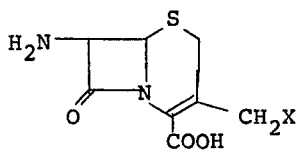

wherein X represents hydrogen, hydroxy, acetoxy or a nucelophilic residual group, which comprises contacting a 7-acylamino-cephem compound of the formula

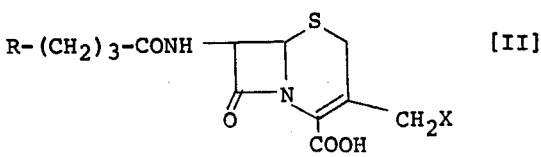

wherein R represents —COOH or —COCOOH and X has the same meaning as above with a microbial culture or preparation thereof containing deacylating enzyme derived from *Comamonas sp.* NRRL B-8070 in an aqueous medium.

* * * * *